United States Patent
David et al.

(10) Patent No.: US 6,649,668 B1
(45) Date of Patent: Nov. 18, 2003

(54) INITIATOR SYSTEM COMPRISING AN ONIUM BORATE AND A CYCLIC GROUP CONTAINING PHOTOINITIATOR

(75) Inventors: Marie-Anne David, Venissieux (FR); Jean-Marc Frances, Meyzieu (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/463,363

(22) PCT Filed: Jul. 22, 1998

(86) PCT No.: PCT/FR98/01620
§ 371 (c)(1),
(2), (4) Date: Jun. 15, 2000

(87) PCT Pub. No.: WO99/05181
PCT Pub. Date: Feb. 4, 1999

(30) Foreign Application Priority Data

Jul. 23, 1997 (FR) ............................................. 97 09379
Jan. 29, 1998 (FR) ............................................. 98 01251

(51) Int. Cl.[7] ........................ C08F 4/52; C09D 163/00; C09D 183/00
(52) U.S. Cl. ........................... 522/15; 522/25; 522/168; 522/169; 522/170; 522/181; 522/148; 522/99; 528/13; 528/33; 528/417; 528/418; 528/421
(58) Field of Search ............................... 522/15, 31, 25, 522/170, 169, 168, 181, 148, 99; 528/421, 417, 418, 33, 13, 5, 4, 7, 6, 8; 526/131, 132, 133, 134; 523/200

(56) References Cited

U.S. PATENT DOCUMENTS 5,340,898 A * 8/1994 Cavezzan et al.
5,693,688 A * 12/1997 Priou
5,703,137 A * 12/1997 Priou et al.
5,952,152 A * 9/1999 Cunningham et al.
6,011,180 A * 1/2000 Cunningham et al.

FOREIGN PATENT DOCUMENTS

EP 0562897 9/1993

* cited by examiner

*Primary Examiner*—Susan W. Berman
(74) *Attorney, Agent, or Firm*—Burns, Doane, Swecker & Mathis, L.L.P.

(57) ABSTRACT

The invention concerns the field of polymerization and/or cross-linking reaction catalysis by cationic process of monomers, oligomers and/or polymers. In particular, novel polymerization and/or cross-linking initiator systems comprising at least one onium borate and at least one benzophenone are described to satisfy the ever greater exigencies of productivity and manufacture. The initiators are used in particular for preparing resins and/or composite materials based on an organic and/or silicon matrix or optionally a matrix of acrylic monomers, oligomers, or polymers.

19 Claims, 2 Drawing Sheets

INITIATOR SYSTEM COMPRISING AN ONIUM BORATE AND A CYCLIC GROUP CONTAINING PHOTOINITIATOR

FIELD OF THE INVENTION

The field of the invention is that of the catalysis of reactions for the cationic polymerization and/or crosslinking of monomers, oligomers and/or polymers, comprising reactive functional radicals capable of forming intra-chain and inter-chain bridges, so as to obtain a polymerized and/or crosslinked composite material or coating which has a certain level of hardness and a certain level of mechanical strength.

More specifically, the subject of the present invention is novel initiator systems for cationic polymerization and/or crosslinking. These initiators comprise at least one onium borate and at least one cyclic compound allowing the initiation and progress of reactions for forming polymers and/or resins, starting with substrates formed from monomers, oligomers and/or polymers containing reactive organofunctional groups.

The reactions more particularly concerned are those in which cationic agents act as direct promoters of inter-chain and/or intra-chain bonding.

In general, these reactions take place by photochemical and/or thermal activation and/or by activation with a beam of electrons. As a practical example, the light energy of a UV radiation allows the formation of active protagonists, for example by cleaving bonds, and thus triggering of the polymerization and/or crosslinking reactions is effected.

In the present description, the polymers and/or resins obtained are prepared from monomers, oligomers and/or polymers which are either (1) of organic nature, in particular exclusively hydrocarbon-based, or (2) of polyorganosiloxane nature, and comprise organofunctional groups in their structure, for example groups such as epoxides, oxetanes and/or alkenyl ethers, which react cationically and with the aid of the novel initiator systems according to the invention which are described below. It is also possible to use (3) monomers, oligomers and/or polymers with acrylic groups, for example pure acrylic or methacrylic groups, which can be added to the cationic polymerization medium.

A subject of the present invention is thus also compositions comprising base materials (monomers, oligomers and/or polymers) which can be polymerized and/or crosslinked cationically, the initiator systems described below, and optionally one or more additives chosen from those generally known in the applications for which these compositions are intended.

For example, these compositions can be used to make coatings on objects such as solid articles or supports, in particular a paper support, a polymer film of polyester or polyolefin type, an aluminium support and/or a tinplate support.

BACKGROUND OF THE INVENTION

Initiators for the polymerization and/or crosslinking, for example the photochemical polymerization and/or crosslinking, of monomers, oligomers and/or polymers comprising reactive organofunctional groups in their structure are described in EP-0 562 897 in the name of the Applicant. The initiator salts in that patent represent an appreciable technical advance over the initiators previously known, of onium salt type or of organometallic complex type, and in particular over those in which the anion of the initiator salt is $SbF_6^-$ which is one of the only types which is satisfactory in terms of catalytic performance, but which poses serious problems of use on account of the presence of heavy metals.

The initiator salts according to EP-A-0 562 897 are used, for example, for the preparation of coatings on paper starting with epoxidized monomers which are polymerized and crosslinked by UV irradiation. In order to assess the performance as initiator, the reactivity of the substrate/initiator couple and the speed of polymerization/crosslinking are evaluated, by means of the rate of throughput required to cure the layer coated onto the paper, as well as by means of the number of passages. The measured results are acceptable, but it nevertheless remains that, in order to satisfy the production efficiency requirements of the people using them, the initiator systems need to achieve higher and higher performance levels. They must thus make it possible to achieve polymerization/cross-linking reactivities and rates that are as high as possible, so as to be able to increase the coating rates.

Accordingly, one of the essential objects of the present invention is to satisfy the production efficiency requirements stated above.

Another essential object of the invention is to provide novel initiator systems which give high performance as initiators with respect to the majority of organofunctional monomers, oligomers and/or polymers which can be polymerized and/or crosslinked cationically; the monomers, oligomers and/or polymers being in particular (1) of organic nature, preferably exclusively hydrocarbon-based, or (2) of polyorganosiloxane nature, optionally as a mixture (3) with other monomers, oligomers and/or polymers containing acrylic groups.

Another essential object of the invention is to provide cationic initiator systems which are effective in small amount, but which are also easy to handle and relatively non-toxic, and which consequently make it possible to obtain composite coatings and/or materials which do not yellow over time and/or after curing.

Another object of the invention is to provide compositions of organofunctional monomers, oligomers and/or polymers which can be crosslinked cationically and under photonic and/or thermal activation and/or under activation with a beam of electrons.

Another object of the invention is to provide compositions of this type which can be used either as a thin layer, the thickness of which is, for example, in the range from 0.1 to 1 µm, or as a thicker layer, the thickness of which is, for example, in the range from a value of greater than one micrometer to several centimeters.

Another object of the invention is to provide compositions of this type for the preparation of a composite material.

DESCRIPTION OF THE INVENTION

These various objects are achieved by the invention which firstly relates, in its first subject, to novel initiator systems comprising at least one carefully selected onium borate and at least one carefully selected cyclic compound. Thus, the initiator system for polymerization and/or crosslinking comprises:

(1) at least one onium borate in which:
(i) the cationic species is chosen from the onium salts of formula (I)

in which formula:

the radicals $R^1$, which may be identical or different, represent a carbocyclic or heterocyclic $C_6$–$C_{20}$ aryl radical, it being possible for the said heterocyclic radical to contain nitrogen and/or sulphur as hetero elements, the radicals $R^2$, which may be identical or different, represent $R^1$, a linear or branched $C_1$–$C_{30}$ alkyl radical or a linear or branched $C_1$–$C_{30}$ alkenyl radical, the said radicals $R^1$ and $R^2$ optionally being substituted with:
- a linear or branched $C_1$–$C_{25}$ alkyl group,
- an alkoxy group $OR^{13}$
- a ketone group —(C=O)—$R^{13}$,
- an ester or carboxylic group —(C=O)—O—$R^{113}$,
- a mercapto group $SR^{13}$,
- a mercapto group $SOR^{13}$,
- $R^{13}$ being a radical chosen from the group consisting of a hydrogen atom, a linear or branched $C_1$–$C_{25}$ alkyl radical, a $C_6$–$C_{30}$ aryl radical and an alkylaryl radical in which the alkyl portion is linear or branched and $C_1$–$C_{25}$ and the aryl portion is $C_6$–$C_{30}$,
- a nitro group,
- a chlorine atom,
- a bromine atom, and/or
- a cyano group, n is an integer ranging from 1 to v+1, v being the valency of iodine, m is an integer with n+m=v+1;

(ii) and in that the anionic borate species has the formula (II):

$$[BX_a R^3_b]^- \quad (II)$$

in which:

a and b are integers such that $0 \leq a \leq 4$, $0 \leq b \leq 4$, and a+b=4, the symbols X, which may be identical or different, represent:
- a halogen atom chosen from chlorine and/or fluorine with $0 \leq a \leq 3$,
- an OH function with $0 \leq a \leq 2$, and the radicals $R^3$, which may be identical or different, represent:
- a phenyl radical substituted with at least one electron-withdrawing group such as —$CF_3$, —$OCF_3$, —$NO_2$, —CN, —$SO_2R^{14}$, —O(C=O)—$R^{14}$, —O—$C_nF_{2n+1}$, —$C_nF_{2n+1}$, n being an integer between 1 and 20, or substituted with at least two halogen atoms, in particular fluorine atoms,
- an aryl radical containing at least two aromatic nuclei, such as biphenyl or naphthyl, optionally substituted with at least one halogen atom, in particular a fluorine atom, or with an electron-withdrawing group such as —$CF_3$, —$OCF_3$, —$NO_2$, —CN, —$SO_2R^{14}$, —O(C=O)—$R^{14}$, $R^{14}$ being —O—$C_nF_{2n+1}$, —$C_nF_{2n+1}$, n being an integer between 1 and 20;

(2) and at least one cyclic compound corresponding to one of the formulae (III) to (VI) below:

formula (III)

in which:

when n 1, $Ar^1$ represents an aryl radical containing from 6 to 18 carbon atoms, a tetrahydronaphthyl, thienyl, pyridyl or furyl radical or a phenyl radical bearing one or more substituents chosen from the group consisting of F, Cl, Br, CN, OH, linear or branched $C_1$–$C_{12}$ alkyls, —$CF^3$, —$OR^6$, —Ophenyl, —$SR^6$, —Sphenyl, —$SO_2$phenyl, —$COOR^6$, —O—($CH_2$—CH=$CH_2$), —O($CH_2H_4$—O)$_m$—H, —O($C_3H_6$O)$_m$—H, m being between 1 and 100, when n=2, $Ar_1$ represents a $C_6$–$C_{12}$ arylene radical or a phenylene-T-phenylene radical, in which T represents —O—, —S—, —$SO_2$— or —$CH_2$—, X represents a group —$OR^7$ or —$OSiR^8(R^9)_2$ or forms, with $R^4$ a group —O—CH($R^{10}$)—, $R_4$ represents a linear or branched $C_1$–$C_8$ alkyl radical which is unsubstituted or bears a group —OH, —$OR^6$, $C_2$–$C_8$ acyloxy, —$COOR^6$, —$CF^3$ or —CN, a $C_3$ or $C_4$ alkenyl radical, a $C_6$ to $C_{18}$ aryl radical or a $C_7$ to $C_9$ phenylalkyl radical, $R^5$ has one of the meanings given for $R^4$ or represents a radical —$CH_2CH_2R^{11}$, or alternatively forms, with $R^4$, a $C_2$–$C_8$ alkylene radical or a $C_3$–$C_9$ oxa-alkylene or aza-alkylene radical, $R^6$ represents a lower alkyl radical containing from 1 to 12 carbon atoms, $R^7$ represents a hydrogen atom, a $C_1$–$C_{12}$ alkyl radical, a $C_2$–$C_6$ alkyl radical bearing a group —OH, —$OR^6$ or —CN, a $C_3$–$C_6$ alkenyl radical, a cyclohexyl or benzyl radical, a phenyl radical optionally substituted with a chlorine atom or a linear or branched $C_1$–$C_{12}$ alkyl radical or a 2-tetrahydropyranyl radical, $R^8$ and $R^9$ are identical or different and each represent a $C_1$–$C_4$ alkyl radical or a phenyl radical, $R^{10}$ represents a hydrogen atom, a $C_1$–$C_8$ alkyl radical or a phenyl radical, $R^{11}$ represents a radical —$CONH_2$, —$CONHR^6$, —$CON(R^6)_2$, —$P(O)(OR^6)_2$ or 2-pyridyl;

formula (IV)

in which:

$Ar^2$ has the same meaning as $Ar^1$ in formula (III) in the case in which n=1, $R^{15}$ represents a radical chosen from the group consisting of a radical $Ar^2$, a radical —(C=O)—$Ar^2$, a linear or branched $C_1$–$C_{12}$ alkyl radical, a $C_6$–$C_{12}$ cycloalkyl radical and a cycloalkyl radical forming a $C_6$–$C_{12}$ ring with the carbon of the ketone or a carbon of the radical $Ar^2$, it being possible for these radicals to be substituted with one or more substituents chosen from the group consisting of —F, —Cl, —Br, —CN, —OH, —$CF_3$, —$OR^6$, —$SR^6$, —$COOR^6$, linear or branched $C_1$–$C_{12}$ alkyl radicals optionally bearing a group —OH, —OR and/or —CN; and linear or branched $C_1$–$C_8$ alkenyl radicals;

formula (V)

in which $Ar^3$ has the same meaning as $Ar^1$ in formula (III) in the case in which n=1, $R^{16}$, which may be identical or different, represent a radical chosen from the group consisting of a radical $Ar^3$, a radical —(C=O)—$Ar^3$, a linear or branched $C_1$–$C_{12}$ alkyl radical, a $C_6$–$C_{12}$ cycloalkyl radical, it being possible for these radicals to be substituted with one or more substituents chosen from the group consisting of —F, —Cl, —Br, —CN, —OH, —$CF_3$, —$OR^6$, —$SR^6$, —$COOR^6$, linear or branched $C_1$–$C_{12}$ alkyl radicals optionally bearing a group —OH, —$OR^6$ and/or —CN, and linear or branched $C_1$–$C_8$ alkenyl radicals;

formula (VI)

in which:

$R^5$, which may be identical or different, have the same meanings as in formula (III), Y, which may be identical or different, represent X and/or $R^4$, Z represents:
- a direct bond,
- a $C_1$–$C_6$ divalent alkylene radical, or a phenylene, diphenylene or phenylene-T-phenylene radical, or alternatively forms, with the two substituents $R^5$ and the two carbon atoms bearing these substituents, a cyclopentane or cyclohexane nucleus,
- a divalent group —O—$R^{12}$—O—, —O—$SiR^8R^9$—O—$SiR^8R^9$—O— or —O—$SiR^8R^9$—O—, $R^{12}$ represents a $C_2$–$C_8$ alkylene, $C_4$–$C_6$ alkenylene or a xylylene radical, and $Ar^4$ has the same meaning as $Ar^1$ in formula (III) in the case in which n=1.

Advantageously, the anionic species of the onium salt is chosen from the following species, alone or as a mixture, of formula: $[B(C_6F_5)_4]^-$, $[B(C_6H_3(CF_3)_2)_4]^-$, $[B(C_6H_4OCF_3)_4]^-$, $[B(C_6H_4CF_3)_4]^-$, $[(C_6F_5)_2BF_2]^-$, $[C_6F_5BF_3]^-$, $[B(C_6H_3F_2)_4]^-$.

More particularly, the anionic species of the onium salt is chosen from the following species, alone or as a mixture, of formulae: $[B(C_6F_5)_4]^-$, $[B(C_6H_3(CF_3)_2)_4]^-$, $[B(C_6H_4OCF_3)_4]^-$.

For the cationic species of the onium borate, this will advantageously be chosen from the group consisting of:

$[(C_6H_5)_2I]^+$, $[C_8H_{17}—O—C_6H_5—I—C_6H_5]^+$,
$[C_{12}H_{25}—C_6H_5—I—C_6H_5]^+$, $[(C_8H_{17}—O—C_6H_5)_2I]^+$,
$[(C_8H_{17})—O—C_6H_5—I—C_6H_5)]^+$, $[(C_{12}H_{25}—C_6H_5)_2I]^+$,
$[(CH(CH_3)_2—C_6H_5)—I—C_6H_5—CH_3]^+$, $[C_6H_4—O—C_6H_4—I—C_6H_4]^+$,
$[C_6H_4—(C=O)—C_6H_4—I—C_6H_4]_+$,
$[C_6H_4—O—C_6H_4—I—C_6H_4—O—C_6H_4]^+$,
$[C_6H_4—(C=O)—C_6H_4—I—C_6H_4—(C=O)—C_6H_4]^{30}$,
$[C_6H_4—I—C_6H_4—O—CH_2—O—CH_2—O—CH(OH)—C_{12}H_{25}]^+$, and a mixture thereof.

The onium borates which form the subject of the present invention can be prepared by exchange reaction between a salt of the cationic species (halide such as, for example, chloride or iodide) with an alkali metal salt of the anionic species (sodium, lithium or potassium).

The operating conditions (respective amounts of reagents, choice of solvents, duration, temperature, stirring) are within the scope of a person skilled in the art; these conditions should make it possible to recover the desired onium borate in solid form by filtering off the precipitate formed, or in oily form by extraction using a suitable solvent.

The operating conditions for synthesizing the halides of the cationic species of formula (I) are known per se. In this respect, reference will be made in particular to patent EP-0 562 897 in the name of the Appplicant.

The procedures for synthesizing the alkali metal salts of the anionic species (II) are also known per se; especially, for example, in patent EP-0 562 897 in the name of the Applicant.

In the context of the invention, many types of cyclic compounds can be used in combination with the onium borate. In this respect, the type of cyclic compound which is used and preferred will depend on the envisaged used, i.e., for example, in the case of activation by UV, its maximum or maxima of absorption of UV light is (are) adapted to the type of application envisaged.

For example, when the composition to be crosslinked and/or polymerized contains white pigments which absorb in the UV range, a cyclic compounds which has a maximum absorption of light in the visible range will be selected.

In the case of a use for the manufacture of transparent organic and/or silicone paint under UV activation, a cyclic compound whose maximum absorption is superposable with the emission lines of the UV lamp will be chosen.

As examples of cyclic compounds, mention will be made in particular of the following products, alone or as a mixture:

9-xanthenone; 1,4-dihydroxyanthraquinone; anthraquinone; 2-methylanthraquinone, 2,2'-bis(3-hydroxy-1,4-naphthoquinone);

2,6-dihydroxyanthraquinone; 1-hydroxycyclohexyl phenyl ketone; 1,5-dihydroxyanthraquinone; 1,3-diphenyl-1,3-propanedione;

5,7-dihydroxyflavone; dibenzoyl peroxide;

2-benzoylbenzoic acid; 2-hydroxy-2-methylpropiophenone; 2-phenylacetophenone;

2,4,6-trimethylbenzoyldiphenylphosphine oxide; anthrone; bis(2,6-dimethylbenzoyl)-2,4,4-trimethylpentylphosphine oxide;

poly[1,4-benzenedicarbonyl-alt-bis(4-phenoxyphenyl) methanone];

and

Preferably, the cyclic compound(s) is (are) chosen from the group consisting of:

4,4'-dimethoxybenzoin; phenanthrenequinone;
2-ethylanthraquinone; 2-methylanthraquinone;
1,8-dihydroxyanthraquinone; dibenzoyl peroxide;
2,2-dimethoxy-2-phenylacetophenone; benzoin;
2-hydroxy-2-methylpropiophenone;
4-(2-hydroxyethoxy)phenyl-(2-hydroxy-2-methylpropyl) ketone;

benzoylacetone;

and a mixture thereof.

As examples of commercial cyclic products, mention may be made of the products sold by the company Ciba-Geigy: Irgacure 369, Irgacure 651, Irgacure 907, Darocure 1173, etc.

The initiator systems according to the invention can be used as they are obtained after the process for preparing them, for example in solid or liquid form or as a solution in a suitable solvent, in compositions of monomers, oligomers and/or polymers which are intended to be polymerized and/or crosslinked cationically and under activation, for example UV activation.

Thus, according to another of its aspects, the invention relates, in its second subject, to compositions comprising at least one matrix based on a monomer, an oligomer and/or a polymer which can be polymerized-and/or crosslinked cationically, a catalytically effective amount of at least one initiator system of the type in accordance with the invention and described above, optionally a polymerization and/or crosslinking accelerator, and optionally also one or more additives chosen from those generally known in the applications for which these compositions are intended.

According to the invention, the expression "effective catalytic amount of initiator" means an amount which is sufficient to initiate the polymerization and/or the crosslinking. This amount is generally between 0.01 and 20 parts by weight, usually between 0.05 and 8 parts by weight, to polymerize and/or crosslink 100 parts by weight of the matrix. In the initiator system according to the invention, the onium borate/cyclic compound weight ratio is between 0.1 and 10.

According to a first advantageous provision of the invention taken in its second subject, the polymerizable and/or crosslinkable composition is based on monomer(s) and/or oligomer(s) and/or polymer(s) of organic nature belonging to at least one of the following organic species:

$\alpha_{1.1}$ cycloaliphatic epoxides, taken alone or as a mixture with each other;
  epoxides such as 3,4-epoxycyclohexylmethyl 3',4-epoxycyclohexanecarboxylate:

or bis(3,4-epoxycyclohexyl) adipate, being particularly preferred;
$\alpha_{1.2}$ non-cycloaliphatic epoxides, taken alone or as a mixture with each other;
  epoxides of the type resulting from the coupling of Bisphenol A and epichlorohydrin and of the type:
    di- and triglycidyl ethers of alkoxylated Bisphenol A, of 1,6-hexanediol, of glycerol, of neopentyl glycol and of trimethylolpropane,
    or Bisphenol A diglycidyl ethers,
  α-olefin epoxides, Novolac epoxide, epoxidized soybean oil and flax oil, epoxidized polybutadiene and, more generally, an epoxidized and monohydroxylated, saturated or unsaturated diene polymer, described in patent application WO-A-96/11215 (the content of which is incorporated in its entirety by way of reference), obtained by epoxidizing a base diene polymer of formula:

$(HO)_x—J—L_z—K—(OH)_y$ or $(HO)_x—J—K—L—(OH)_y$ in which:
    the symbols J and K represent sequences or blocks consisting of: homopolymers obtained by polymerizing a conjugated diene monomer containing from 4 to 24 carbon atoms (such as, for example: 1,3-butadiene, isoprene or 2-methyl-1,3-butadiene, 2-phenyl-1,3-butadiene, 1,3-pentadiene, 3,4-dimethyl-1,3-hexadiene, 4,5-diethyl-1,3-octadiene); copolymers obtained by copolymerizing at least two of the abovementioned conjugated dienes with each other; or copolymers obtained by copolymerizing at least one of the abovementioned conjugated dienes with at least one ethylenically unsaturated monomer chosen from aromatic vinyl monomers containing from 8 to 20 carbon atoms (such as, for example: styrene, ortho-, meta- or para-methylstyrene, vinylmesitylene, vinylnaphthalene);
    the symbol L represents a polymer sequence or block obtained from the abovementioned aromatic vinyl monomers;
    x and y are numbers equal to zero or 1, x being equal to zero when y=1 and x being equal to 1 when y=0; and z is a number equal to zero or 1;
      it being possible for the said base diene polymer, on the one hand before epoxidation, to be partially saturated by hydrogenation, and, on the other hand after epoxidation, to contain from 0.1 to 7 milliequivalents of epoxy function per gram of epoxidized and monohydroxylated diene polymer [as examples of epoxidized and monohydroxylated diene polymers mention will be made of the species obtained by epoxidizing the following base diene polymers: Is—Bu—OH, Is—St/Bu—OH, Is—EtBu—OH or Is—St/EtBu—OH, in which: the symbol Is is a polyisoprene block, the symbol Bu is a polybutadiene block, the symbol EtBu is a poly(ethylene-butylene) block (derived from the selective hydrogenation of a polybutadiene block), the symbol St is a polystyrene block (the St/Bu assembly representing a block based on a random copolymer obtained by copolymerizing 1,3-butadiene and styrene), and OH is a hydroxyl group (the —EtBu—OH assembly meaning, for example, that the hydroxyl-group donor is attached to the hydrogenated polybutadiene block)], being particularly preferred;

$\alpha_2$ linear or cyclic alkenyl ethers, taken alone or as a mixture with each other:

vinyl ethers, in particular triethylene glycol divinyl ether, cyclic vinyl ethers or tetramers and/or dimers of acroleins, and the vinyl ether of the following formula:

propenyl ethers, and butenyl ethers being more especially preferred, $\alpha_3$ polyols, taken alone or as a mixture with each other, and preferably the compound of formula below, I being greater than 1 and less than 100:

in which $R^{16}$ is a linear or branched $C_1$–$C_{30}$ alkyl radical.

According to a second advantageous provision of the invention, taken in its second subject, the polymerizable and/or crosslinkable composition is based on monomer(s) and/or oligomer(s) and/or polymer(s) of polyorganosiloxane nature consisting of units of formula (VII) and ending with units of formula (VIII), or of cyclic nature consisting of units of formula (VII), which are represented below:

(VII)

(VIII)

in which:

the symbols $R^{17}$ are identical or different and represent:
a linear or branched alkyl radical containing 1 to 8 carbon atoms, optionally substituted with at least one halogen, preferably fluorine, the alkyl radicals preferably being methyl, ethyl, propyl, octyl and 3,3,3-trifluoropropyl,
a cycloalkyl radical containing between 5 and 8 optionally substituted cyclic carbon atoms,
an aryl radical containing between 6 and 12 carbon atoms which may be substituted, preferably phenyl or dichlorophenyl,
an aralkyl radical with an alkyl portion containing between 5 and 14 carbon atoms and an aryl portion containing between 6 and 12 carbon atoms, optionally substituted on the aryl portion with halogens, alkyls and/or alkoxys containing 1 to 3 carbon atoms, the symbols Y' are identical or different and represent:
the group $R^{17}$,
a hydrogen radical,
and/or an organofunctional group which can be crosslinked cationically, preferably an epoxy-functional and/or vinyloxy-functional group, connected to the silicon of the polyorganosiloxane via a divalent radical containing from 2 to 20 carbon atoms which can contain at least one hetero atom, preferably oxygen, and
at least one of the symbols Y' representing a functional organic group which can be crosslinked cationically; and the symbol $R^{16}$, which may be identical or different, represents a radical selected from the group consisting of a radical $Ar^3$, a radical —(C=O)—$Ar^3$, a linear or branched $C_1$–$C_{12}$ alkyl radical, a $C_6$–$C_{12}$ cycloalkyl radical, wherein said radical is optionally substituted with one or more substituents selected from the group consisting of —F, —Cl, —Br, —CN, —OH, —CF$_3$, $OR^6$, —$SR^6$, —$COOR^6$, linear or branched $C_1$–$C_{12}$ alkyl radicals optionally bearing a group —OH, —$OR^6$, and/or —CN, and linear or branched $C_1$–$C_8$ alkenyl radicals.

According to one advantageous variant of the invention, at least one of the symbols $R^{17}$ of the polyorganosiloxanes used in the context of the invention as monomer(s), oligomer(s) or polymer(s) represents a phenyl, tolyl or dichlorophenyl radical.

According to another advantageous variant of the invention, the polyorganosiloxanes used comprise from 1 to 10 organofunctional groups per mole. For an epoxy-functional group, this corresponds to epoxide contents ranging from 20 to 2000 molar meq/100 g of polyorganosiloxane.

The linear polyorganosiloxanes can be oils with a dynamic viscosity at 25° C. of about 10 to 10,000 mPa·s at 25° C., generally from about 50 to 5000 mPa·s at 25° C. and even more preferably from 100 to 600 mPa·s at 25° C., or gums with a molecular mass of about 1,000,000.

When the polyorganosiloxanes are cyclic, they consist of units (VII) which can be, for example, of the dialkylsiloxy or alkylarylsiloxy type. These cyclic polyorganosiloxanes have a viscosity of about 1 to 5000 mPa·s.

As examples of divalent radicals linking an organofunctional group of the epoxy type, mention may be made of those included in the following formulae:

As regards organofunctional groups of the alkenyl ether type, mention may be made of those contained in the following formulae:

in which:
$R^{18}$ represents:
an optionally substituted, linear or branched $C_1$–$C_{12}$ alkylene radical, or
a $C_5$–$C_{12}$ arylene radical, preferably a phenylene radical, which is optionally substituted, preferably with one to three $C_1$–$C_6$ alkyl groups,
$R^{19}$ represents a linear or branched $C_1$–$C_6$ alkyl radical.

According to a third other advantageous provision of the invention, taken in its second subject, the polymerizable and/or crosslinkable composition is based on monomer(s) and/or oligomer(s) and/or polymer(s), of polyorganosiloxane nature and of organic nature, in particular hydrocarbon-based.

According to a fourth other advantageous provision of the invention, taken in its second subject, the polymerizable and/or crosslinkable composition is based on monomner(s) and/or oligomer(s) and/or polymer(s), of polyorganosiloxane nature and/or of organic nature, in particular hydrocarbon-based, and also comprises monomers, oligomers and/or polymers containing organofunctional groups of acrylate species; and in particular epoxidized acrylates, acrylo-glycero-polyester, multifunctional acrylates, acrylo-urethanes, acrylo-polyethers, acrylo-polyesters, unsaturated polyesters and acrylo-acrylics.

These acrylic species, optionally as a mixture, which can be used with monomer(s) and/or oligomer(s) and/or polymer (s) of polyorganosiloxane nature and/or of organic nature, are preferably chosen from the following species: trimethylolpropane triacrylate, tripropylene glycol diacrylate, glycidylpropyl triacrylate, pentaerythrityl triacrylate, trimethylolpropane ethoxylate triacrylate, Bisphenol A ethoxylate diacrylate, tripropylene glycol diacrylate, triethylene glycol diacrylate, tetraethylene glycol diacrylate, polyether acrylates, polyester acrylates (for example the product Ebecryl 810 from the company UCB-Radcure) and epoxy acrylates (for example the product Ebecryl 600 from the company UCB-Radcure).

It is recalled that, in the present specification, the expression "acrylic" encompasses compounds comprising the function of the type $CH_2=CH-COO-$ or of the type $CH_2=C(CH_3)-COO-$.

Conventionally, the compositions according to the invention, taken in its second subject, can also comprise one or more additives chosen as a function of the final intended application.

When the polymerizable and/or crosslinkable composition is based on at least one of the organic species $\alpha_{1.1}$ to $\alpha_3$, optionally as a mixture with monomers, oligomers and/or polymers of acrylic nature, the additives can especially be compounds optionally in the form of polymers, with labile hydrogens, such as alcohols, glycols and polyols, which are useful for improving the flexibility of the cured material after polymerization and/or crosslinking; mention may be made, for example, of polycaprolactone-polyols, in particular the polymer obtained from 2-ethyl-2-(hydroxymethyl)-1,3-propanediol and from 2-oxepanone, such as the product Ton Polyol-301 sold by the company Union Carbide, or the other commercial polymers Tone Polyol 201 and Tone Polyol 12703 from the company Union Carbide. In addition, in this case, additives which may be mentioned are diacids containing a long alkyl chain, epoxidized or non-epoxidized unsaturated fatty acid esters, for example epoxidized soybean oil or epoxidized flax oil, the epoxidized 2-ethylhexyl ester, 2-ethylhexyl epoxystearate, octyl expoxystearate, epoxidized acrylic esters, epoxidized soybean oil acrylates, epoxidized flax oil acrylates, polypropylene glycol diglycidyl ether, epoxides containing long aliphatic chains, etc.

They may also be, irrespective of the nature of the polymerizable matrix, for example: mineral fillers such as, in particular, ground synthetic (polymer) or natural fibres, calcium carbonate, talc, clay, titanium dioxide, precipitation or combustion silica; photosensitizers, in particular based on thioxanthone (for example: isopropylthioxanthone, diethylthioxanthone and 1-chloro-4-propoxythio-xanthone); soluble dyes; oxidation inhibitors and corrosion inhibitors; organosilicon or non-organosilicon adhesion modifiers; fungicidal, bactericidal or antimicrobial agents; and/or any other material which does not interfere with the catalytic activity of the initiator and which does not absorb in the wavelength range chosen for the photoactivation.

The examples and tests below are given for illustrative purposes. They will make it possible in particular to gain a clearer understanding of the invention and to allow all of its advantages to emerge and to see a number of its embodiments.

EXAMPLES and TESTS

The products used in the examples are the following:

(H1)

a = 70; b = 7

(M1)

(P2)

(PS1)

M1 is a product sold under the reference UVR6105 or UVR6110 by the company Union Carbide.

P1 is the initiator of onium borate type and P2 is the initiator of cyclic type. 1-Chloro-4-propoxythioxanthone is used as photosensitizer PS1.

The alcohol T1 used is the product Tone Polyol 301 from the company Union Carbide.

Example 1

Preparation of White Inks

A concentrated pigment base ("CPB") is obtained by dispersing 600 parts of rutile titanium oxide sold under the reference R960 by the company Dupont de Nemours, and 400 parts of cycloaliphatic epoxy resin M1 in a 2 liter reactor fitted with a central three-paddle stirrer.

The concentrated pigment base is obtained by mixing for 30 min with the titanium oxide powder poured beforehand onto the resin M1 preheated to 40° C.

The pigment base is then ground on a three-roller mill so as to obtain a dispersion whose particle size is less than 10 μm.

This pigment base is stable on storage. At a temperature which may be between −20° C. and 100° C., its properties are not affected for several months.

Four initiator solutions are prepared:

| Reagents | Solution 1 | Solution 2 | Solution 3 | Solution 4 |
|---|---|---|---|---|
| P1 | 9.4 | 9.6 | 8 | 7.5 |
| P2 | 0 | 9.6 | 9.5 | 7.5 |
| PS1 | 9.4 | 9.6 | 9.5 | 9 |
| Isopropanol | 15.6 | 4.8 | | 0 |
| M1 | 65.6 | 66.4 | 68.2 | 76 |

Starting with these four initiator solutions, four white ink formulations are prepared:

| Reagents | Formulation 1 | Formulation 2 | Formulation 3 | Formulation 4 |
|---|---|---|---|---|
| Solution 1 | 6.4 | 0 | 0 | 0 |
| Solution 2 | 0 | 6.3 | 0 | 0 |
| Solution 3 | 0 | 0 | 6.3 | 0 |
| Solution 4 | 0 | 0 | 0 | 6.6 |
| M1 | 6.4 | 6.5 | 6.5 | 6.2 |
| CPB | 81.7 | 81.7 | 81.7 | 81.7 |
| Ti | 4 | 4 | 4 | 4 |
| BYK361* | 1.5 | 1.5 | 1.5 | 1.5 |
| Total | 100 | 100 | 100 | 100 |
| P1% | 0.6 | 0.6 | 0.5 | 0.5 |

(*Surfactant sold by the company Byk)

The drying of the inks is evaluated on a UV block from the company IST fitted with two lamps with a power rating of 200 W/cm: a gallium-doped mercury lamp and an undoped mercury lamp working at maximum power.

Test 1

Resistance to Solvents of the White Inks Formulated in Example 1

The resistance to solvents of the inks obtained is measured after drying 12 μm films on a manual coating bar of reference No. 2 from the company Erichsen, noting the number of to-and-fro cycles required, carried out using a cloth soaked with solvent to disintegrate the ink layer after drying for 24 hours.

The solvent used is methyl ethyl ketone (MEK).

The adhesion of the layers of ink is measured according to the standardized "crosshatch NFT30-038" test.

| Reagents (%) | Formulation 1 | Formulation 2 | Formulation 3 | Formulation 4 |
|---|---|---|---|---|
| Limit speed (m/min) | 7 | 40 | 25 | 30 |
| V (m/min) | 3 | 15 | 10 | 15 |
| MEK | >100 | >100 | >100 | >100 |
| Adhesion* | 0 | 0 | 0 | 0 |

Formulation 1 containing no radical initiator P2 is very difficult to dry.

Formulations 2, 3 and 4 comprising the initiator system P1 and P2 dry at much faster speeds, which makes them particularly suitable, for example, for use on a production line for manufacturing aerosol cans.

For comparative purposes, formulations 1 and 4 were prepared, replacing the initiator P1 with the photoinitiator P3:

For formulations 1 and 4 with the initiator P3, no drying is observed for concentrations identical to that of P1.

In order to obtain correct drying, a concentration of photoinitiator P3 of at least greater than 1.5% by weight is required, with or without radical initiator P2.

In addition, the coatings obtained with a concentration of photoinitiator P3 of greater than 1.5% by weight are coloured (pink colour).

The photoinitiator P3 thus performs less well than the photoinitiator P1, the acid released under radiation from the antimony salt performing considerably less well than in the case of the borate anion. In addition, the addition of cyclic compound P2 does not improve the performance qualities of the initiator P3, in contrast with the optimized performance levels of the couple P1 and P2.

Example 2

Preparation of Epoxy Resins

Formulations of epoxy resins for composite materials are obtained by mixing an initiator solution P1, P2 and the photosensitizer PS1 with a resin M2.

The epoxy resin M2 is based on Bisphenol A diglycidyl ether and its higher homologues obtained by coupling Bisphenol A with epichlorohydrin.

The resin M2 of viscosity 20,000 mPa·s is diluted with 13% isopropanol or 13% methyl ethyl ketone in order to lower its viscosity to about 300 mPa·s.

5.51 parts of an initiator solution containing 9.07% P1; 9.07% PS1; 9.07% P2 and 72.8% resin M1 are added to 100 parts of resin M2.

The whole is mixed together in order to obtain a uniform mixture.

Six pieces of glass fabric of 300 g/M2 are then impregnated with the resin containing the initiator solution so as to obtain, after evaporation of the solvent for 30 min under a vacuum of 100 mmHg and at 80° C., a degree of impregnation of between 30 and 50%.

At this stage, the pieces of preimpregnated fabric obtained are stable at room temperature and under protection from the light for several days, i.e. no polymerization is observed.

The preimpregnated pieces of fabric are then dried under UV without subsequent heat treatment or with subsequent heat treatment.

A. Drying With Heat Treatment

A UV dose as described in Example 1 is applied to each face of 6 preimpregnated fabrics, for a throughput speed of the UV block of 30 m/min.

The 6 fabrics are then stacked and the stack is pressed for 10 minutes at 90° C. under $5 \times 10^5$ pascals.

After removing from the mould, a composite material with a thickness of about 2 mm is obtained, the glass transition temperature of which, measured by differential calorimetric analysis, is 120° C.

The degree of residual unreacted epoxides is also visualized by measuring any heat of reaction.

After several reproducibility tests, a degree of residual epoxides of less than 10% and usually less than 5% is recorded.

B. Drying Under UV Alone

The 6 squares of impregnated glass fabric are maintained pressed on a stainless steel plate between two sheets of polyester by applying to the squares a vacuum of 100 mmHg.

The assembly maintained under vacuum is then irradiated through the polyester sheet for five seconds with two lamps. The first lamp is a 200 W/cm Hg/Ga lamp used at full power and the second lamp is a 200 W/cm Hg lamp working at 80 W/cm so as not to cause excessive surface drying.

After cooling to room temperature, a composite material is obtained whose glass transition temperature is in the region of 120° C. and which contains less than 10% of residual epoxide functions.

Example 3

Preparation of Compositions for Organic Paint and Evaluation on a UV Block

The crosslinking of formulations 5 and 6 below is studied:

| Reagents | Formulation 5 | Formulation 6 |
|---|---|---|
| Resin M1 | 84 parts | 84 parts |
| Alcohol T1 | 15 parts | 15 parts |
| Surfactant BYK361 | 1 part | 1 part |
| P1 | 0.25 part | 0.25 part |

-continued

| Reagents | Formulation 5 | Formulation 6 |
|---|---|---|
| P2 | 1 part | 0 part |
| Isopropanol | 0 part | 1 part |

A. The crosslinking is carried out on a layer 2 mm thick using a high pressure mercury arc lamp connected to an optical fibre of diameter 8 mm, sold by the company EFOS (Ultracure 100SS).

The optical fibre is connected to the measuring cuvette of a Rapra "Vibrating Needle Curemeter" (VNC) machine. The vibrating needle dips into the epoxy matrix (1 cm$^3$) and a potential difference is measured according to the degree of crosslinking at a given vibration frequency which is 40 Hz.

When irradiated, the medium reaches the congelation point very quickly. This is reflected by a variation in the measured potential. The curve of potential variation is recorded throughout the UV exposure and the value of the time which corresponds to 95% of the total variation (=T95) is reported.

Figure 1:
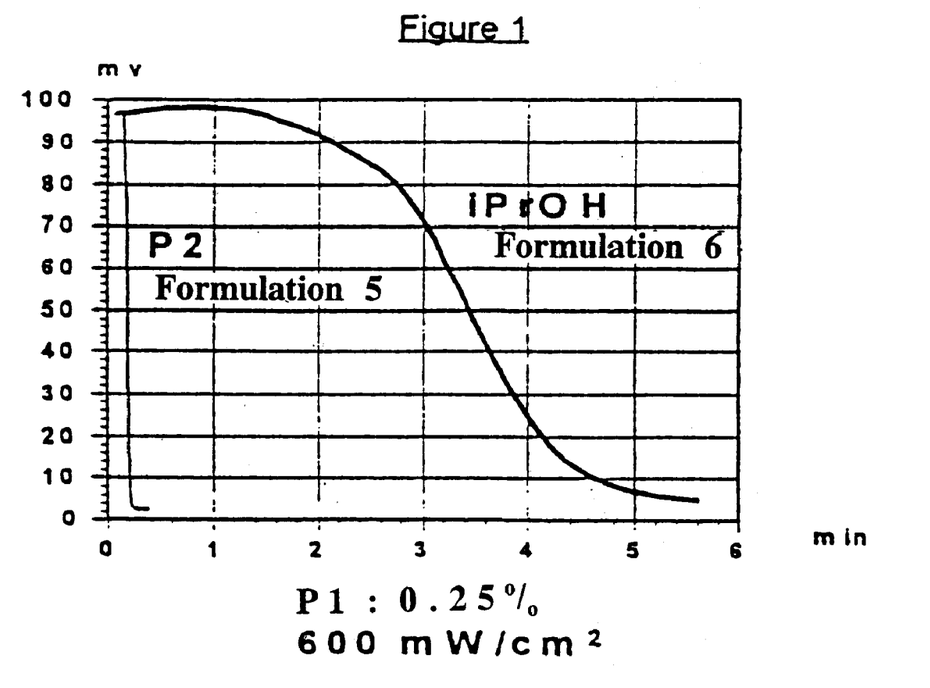
FIG. 1 is a graph showing the results recorded with the Rapra machine in a thick layer for formulations 5 and 6.

In the context of our tests, FIG. 1 below indicates the results recorded with the Rapra machine in a thick layer for formulations 5 and 6. According to this figure, the T95 value for formulation S with the cyclic compound P2 is very much lower than that for formulation 6 without cyclic compound P2, which means that the initiator system P2 and P1 greatly activates the crosslinking.

Figure 2:
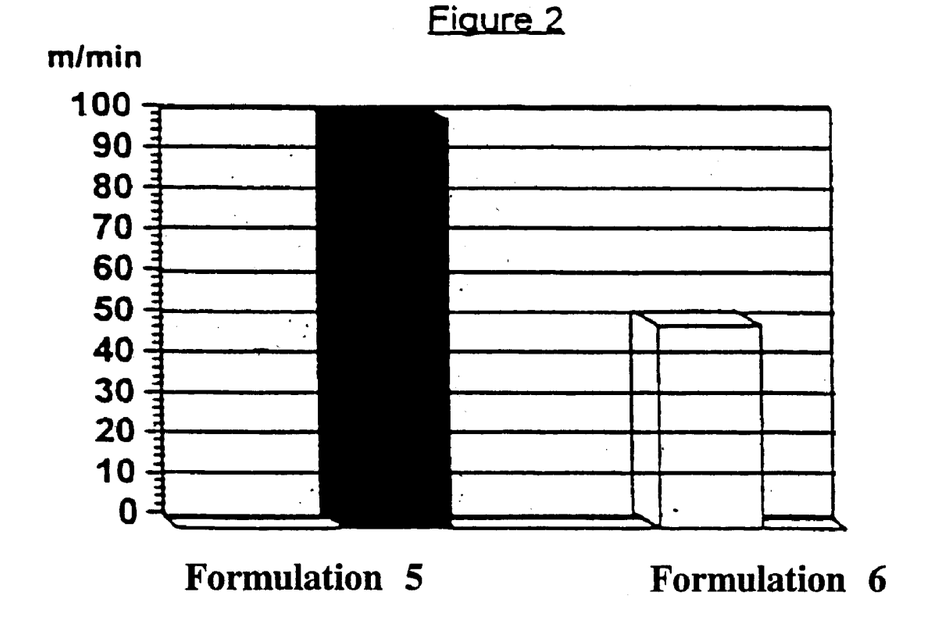
FIG. 2 is a bar graph showing the drying speed for formulations 5 and 6.

Films 12 μm thick were prepared with a polyester support on a manual coating bar of reference No. 2 from the company Erichsen. The results lead to the same conclusions as before, i.e. the cyclic compound P2 and onium borate P1 system greatly accelerates the crosslinking; specifically, in accordance with FIG. 2, the drying speed for formulation 5 is twice as high as that for formulation 6.

Example 4

Preparation of a Composition for Silicone Paint and Evaluation on a UV Block

A formulation 7 of photo-crosslinkable silicone is prepared by mixing together 100 parts of a silicone oil H1 with two parts of a solution containing 20% initiator P1 in the initiator P2.

This formulation 7 is homogenized for 5 minutes by magnetic stirring.

The drying potential of this formulation 7 is then evaluated in the form of a 1 micrometer coating on a paper of glassine type (Sibille) with a throughput speed of 100 m/min in the presence of a mercury arc UV source with a power rating of 120 W/cm. This gives:
  a dose of 0.05 J/cm$^2$: UV-A (320–390 nm)
  a dose of 0.04 J/cm$^2$: UV-B (280–320 nm), and
  a dose of 0.005 J/cm$^2$, UV-C (250–260 nm).

The silicone formulation 7 dries perfectly and no trace is observed with the finger. The coating obtained shows no tendency towards gumming when subjected to a friction test with the index finger for more than ten to-and-fro cycles.

For comparative purposes, a silicone formulation 7' is prepared without initiator P2, by mixing together 100 parts of a silicone oil Hi with two parts of a solution containing 20% initiator P2 in isopropanol. The drying obtained is good, but a marked tendency towards gumming is observed when the silicone support is subjected to the friction test with the index finger.

Example 5

Composition for Silicone Paint and Evaluation of its Degree of Crosslinking

The silicone-based composition is identical to that of formulation 7. For comparative purposes, a formulation 7" without initiator P2 is prepared by mixing together 100 parts of a silicone oil H1 with 2 parts of a solution containing 20% initiator P2 in diacetone alcohol.

The tests were carried out using a paper-coating machine fitted with a Fusion H lamp working at 120 W/cm.

i) After coating on paper of glassine type (Sibille) at a rate of 100 m/min, the hexane-extractable materials are measured. For formulation 7, only 4% extractable materials are obtained, whereas for formulation 7", 11.3% extractable materials are obtained: this means that the crosslinking of the coating is greater using formulation 7.

ii) The coated papers obtained using formulation 7 and formulation 7", respectively, are then placed in contact with an adhesive paper Tesa 4970. The peeling forces were measured after 20 hours and 6 days at a temperature of 70° C.

For the paper coated using formulation 7, the peeling force is 30 g/m after 20 hours, and 40 g/m after 6 days.

For the paper coated using formulation 7", the peeling force is 30 g/m after 20 hours, and 80 g/m after 6 days.

Example 6

Composition for Silicone Paint and Evaluation on a UV Block

1) Preparation of the Following Initiator Solutions:

| Ingredients (i) | Solution A | Solution B | Solution C | Solution D |
|---|---|---|---|---|
| P1 (2) | 20 | — | 10.45 | — |
| P4 (3) | — | 20 | — | 20 |
| P2 (4) | — | — | 20.90 | 40 |
| Solvent | methyl ethyl ketone 80 | methyl ethyl ketone 80 | diisopropyl-naphthalene 68.65 | methyl ethyl ketone 40 |

(1) The various proportions are expressed as parts by weight (2) Initiator of onium borate type whose formula is given above (3) Initiator of onium borate type whose formula is:

(P4)

(4) Initiator containing a benzoyl radical whose formula is given above.

2) Using These Four Initiator Solutions, Four Organic Paint Formulations (Numbered 8, 9, 10 and 11) are Prepared:

| Ingredients (5) | Formulation 8 (control) | Formulation 9 (control) | Formulation 10 | Formulation 11 |
|---|---|---|---|---|
| Epoxy resin M3 (6) | 80 | 80 | 80 | 84 |
| Diisopropyl-naphthalene | 20 | 20 | 20 | 16 |
| Solution (A, B, C or D) | Solution A | Solution B | Solution C | Solution D |
|  | 2 | 2 | 4 | 2 |
| P1 (7) | 0.5% | — | 0.52% | — |
| P4 (7) | — | 0.5% | — | 0.48% |
| P2 (7) | — | — | 1.05% | 0.95% |

(5) The various proportions are expressed as parts by weight (6) Linear, epoxidized and monohydroxylated diene polymer, obtained by epoxidizing the base diene polymer of structure Is—EtBu—OH, containing 1.49 milliequivalents of epoxide function and 0.17 milliequivalent of OH function per gram; this epoxidized and hydroxylated diene polymer is sold by the company Shell under the name Kraton® EKP 207.

(7) The weight percentage of initiator is indicated here, expressed relative to the matrix M3 to be photopolymerized.

Tests of crosslinking as a 2 mm thick layer are carried out on a Rapra machine, reproducing the procedure described above in Example 3, Section A.

The results obtained, expressed in terms of T95, are collated in the following table:

| Formulation | 8 | 9 | 10 | 11 |
|---|---|---|---|---|
| T95 in minutes | 1.5 | 1.6 | 0.5 | 1 |

It can be seen that the use of the co-initiator containing a benzoyl radical P2 greatly activates the initiators P1 (formulation 10) and P4 (formulation 11).

3) Test of Reactivity as a Thin Layer:

Solution C described above in §1) is used in a proportion of 1 part by weight per 100 parts by weight of epoxide matrix M3. It is mixed with the photoinitiator system so as to obtain a clear mixture.

A film 12 µm thick applied to a sheet of aluminium 0.1 mm thick is dried using a conveyor equipped with a mercury arc lamp operating at 80 W/cm at a speed of 100 m/min. The product leaving the machine has a tack-free surface.

A comparative test is carried out in the absence of initiator P2 containing benzoyl radicals, using solution A. The product leaving the machine has a tacky surface.

What is claimed is:

1. Initiator system for polymerization and/or crosslinking, comprising:

(1) at least one onium borate in which:

(i) the cationic species is an onium salt of formula (I)

$$[(R^1)_n\text{—I—}(R^2)_m]^+ \qquad (I)$$

in which formula:

the radicals $R^1$, which may be identical or different, represent a carbocyclic or heterocyclic $C_6$–$C_{20}$ aryl radical, the radicals $R^2$, which may be identical or different, represent $R^1$, a linear or branched $C_1$–$C_{30}$ alkyl radical or a linear or branched $C_1$–$C_{30}$ alkenyl radical, said radicals $R^1$ and $R^2$ optionally being substituted with:

a linear or branched $C_1$–$C_{25}$ alkyl group,
an alkoxy group $OR^{13}$,
a ketone group —(C=O)—$R^{13}$,
an ester or carboxylic group —(C=O)—O—$R^{13}$,
a mercapto group $SR^{13}$,
a mercapto group $SOR^{13}$,
$R^{13}$ being a radical selected from the group consisting of a hydrogen atom, a linear or branched $C_1$–$C_{25}$, alkyl radical, a $C_6$–$C_{30}$ aryl radical and an alkylaryl radical in which the alkyl portion is linear or branched and $C_1$–$C_{23}$ and the aryl portion is $C_6$–$C_{30}$,
a nitro group,
a chlorine atom,
a bromine atom, and/or
a cyano group, n is an integer ranging from 1 to v+1, v being the valency of iodine, m is an integer with n+m=v+1;

(ii) and the anionic borate species has the formula (II):

$$[BX_a R^3_b]^- \qquad (II)$$

in which:

a and b are integers such that $0 \leq a \leq 4$, $0 \leq b \leq 4$, and a+b=4, the symbols X, which may be identical or different, represent:

a halogen atom chosen from chlorine and/or fluorine with $0 \leq a \leq 3$,
an OH function with $0 \leq a \leq 2$, and the radicals $R^3$, which may be identical or different, represent:

a phenyl radical substituted with at least one electron-withdrawing group or substituted with at least two halogen atoms,
an aryl radical containing at least two aromatic nuclei, optionally substituted with at least one halogen atom, or with an electron-withdrawing group;

(2) and at least one cyclic compound corresponding to one of the formulae (III) to (VI) below:

formula (III)

in which:

when n=1, $Ar_1$ represents an aryl radical containing from 6 to 18 carbon atoms, a tetrahydronaphthyl, thienyl, pyridyl or furyl radical or a phenyl radical bearing one or more substituents selected from the group consisting of F, Cl, Br, CN, OH, linear or branched $C_1$–$C_{12}$ alkyls, —$CF^3$, —$OR^6$, —Ophenyl, —$SR^6$, —Sphenyl, —$SO_2$phenyl, —$COOR^6$, —O—(CH$_2$—CH=CH$_2$), —O(CH$_2$H$_4$—O)$_m$—H, and —O(C$_3$H$_6$O)$_m$—H, m being 1 and 100, when n=2, $Ar^1$ represents a $C_6$–$C_{12}$ arylene radical or a phenylene-T-phenylene radical, in which T represents —O—, —S—, —$SO_2$— or —$CH_2$—, X represents a group —$OR^7$ or —$OSiR^9(R^9)2$ or forms, with $R^4$, a group —O—CH($R^{10}$)—, $R^4$ represents a linear or branched $C_1$–$C_8$ alkyl radical which is unsubstituted or bears a group —OH, —$OR^6$, $C_2$–$C_8$ acyloxy, —$COOR^6$, —$CF^3$ or —CN, a $C_3$ or $C_4$ alkenyl radical, a $C_6$ to $C_{18}$ aryl radical or a $C_7$ to $C_9$ phenylalkyl radical, $R^5$ has one of the meanings given for $R^4$ or represents a radical —$CH_2CH_2R^{11}$, or alternatively forms, with $R^4$, a $C_2$–$C_8$ alkylene radical or a $C_3$–$C_9$ oxa-alkylene or aza-alkylene radical,

$R^6$ represents a lower alkyl radical containing from 1 to 12 carbon atoms, $R^7$ represents a hydrogen atom, a $C_1$–$C_{12}$ alkyl radical, a $C_2$–$C_6$ alkyl radical bearing a group —OH, —$OR^6$ or —CN, a $C_3$–$C_6$ alkenyl radical, a cyclohexyl or benzyl radical, a phenyl radical optionally substituted with a chlorine atom or a linear or branched $C_1$–$C_{12}$ alkyl radical or a 2-tetrahydropyranyl radical, $R^8$ and $R^9$ are identical or different and each represent a $C_1$–$C_4$ alkyl radical or a phenyl radical, $R^{10}$ represents a hydrogen atom, a $C_1$–$C_8$ alkyl radical or a phenyl radical, $R^{11}$ represents a radical —$CONH_2$, —$CONHR^6$, —$CON(R^6)_2$, —$P(O)(OR^6)_2$ or 2-pyridyl;

formula (IV)

in which:

$Ar^2$ has the same meaning as $Ar^1$ in formula (III) in the case in which n=1, $R^{15}$ is selected from the group consisting of a radical $Ar^2$, a radical —(C=O)—$Ar^2$, a linear or branched $C_1$–$C_{12}$ alkyl radical, a $C_6$–$C_{12}$ cycloalkyl radical and a cycloalkyl radical forming a $C_6$–$C_{12}$ ring with the carbon of the ketone or a carbon of the radical $Ar^2$, it being possible for these radicals to be substituted with one or more substituents selected from the group consisting of —F, —Cl, —Br, —CN, —OH, —$CF_3$, —$OR^6$, —$SR^6$, —$COOR^6$, linear or branched $C_1$–$C_{12}$ alkyl radicals optionally bearing a group —OH, —$OR^6$ and/or —CN; and linear or branched $C_1$–$C_8$ alkenyl radicals;

formula (V)

in which $Ar^3$ has the same meaning as $Ar^1$ in formula (III) in the case in which n=1, $R^{16}$, which may be identical or different, is selected from the group consisting of a radical $Ar^3$, a radical —(C=O)—$Ar^3$, a linear or branched $C_1$–$C_{12}$ alkyl radical, and a $C_6$–$C_{12}$ cycloalkyl radical, it being possible for these radicals to be substituted with one or more substituents selected from the group consisting of —F, —Cl, —Br, —CN, —OH, —$CF_3$, —$OR^6$, —$SR^6$, —$COOR^6$, linear or branched $C_1$–$C_{12}$ alkyl radicals optionally bearing a group —OH, —$OR^6$ and/or —CN; and linear or branched $C_1$–$C_8$ alkenyl radicals;

formula (VI)

in which:

$R^5$, which may be identical or different, has the same meaning as in formula (III), Y, which may be identical or different, represent X and/or $R^4$, Z represents:
  a direct bond,
  a $C_1$–$C_6$ divalent alkylene radical, or a phenylene, diphenylene or phenylene-T-phenylene radical, or alternatively forms, with the two substituents $R^5$ and the two carbon atoms bearing these substituents, a cyclopentane or cyclohexane nucleus,
  a divalent group —O—$R^{12}$—O—, —O—$SiR^8R^9$—O—$SiR^8R^9$—O— or —O—$SiR^8R^9$—O—, $R^{12}$ represents a $C_2$–$C_8$ alkylene, $C_4$–$C_6$ alkenylene or a xylylene radical, and $AR^4$ has the same meaning as $Ar^1$ in formula (III) in the case in which n=1, wherein the weight ratio of onium borate to cyclic compound is between 0.1 and 10.

2. Initiator system according to claim 1, wherein the anionic species of the onium borate comprises [$B(C_6F_5)_4$]⁻, [$B(C_6H_3)(CF_3)_2)_4$]⁻, [$B(C_6H_4OCF_3)_4$]⁻, [$B(C_6H_4CF_3)_4$]⁻, [$(C_6F_5)_2BF_2$]⁻, [$C_6F_5BF_3$]⁻, [$B(C_6H_3F_2)_4$]⁻, or a mixture thereof.

3. Initiator system according to claim 1, wherein the anionic species of the onium salt comprises [$B(C_6F_5)_4$]⁻, [$B(C_6H_3(CF_3)_2)_4$]⁻, [$B(C_6H_4OCF_3)_4$]⁻, or a mixture thereof.

4. Initiator system according to claim 1, wherein the cationic species of the onium borate comprises:

[$(C_6H_5)_2I$]⁺, [$C_8H_{17}$—O—$C_6H_5$—I—$C_6H_5$]⁺, [$C_{12}H_{25}$—$C_6H_5$—I—$C_6H_5$]⁺, [$(C_8H_{17}$—O—$C_6H_5)_2I$]⁺, [$(C_8H_{17})$—O—$C_6H_5$—I—$C_6H_5)$]⁺, [$(C_{12}H_{25}$—$C_6H_5)_2I$]⁺, [$(CH(CH_3)_2$—$C_6H_5)$—I—$C_6H_5$—$CH_3$]⁺, [$C_6H_4$—O—$C_6H_4$—I—$C_6H_4$]⁺, [$C_6H_4$—(C=O)—$C_6H_4$—I—$C_6H_4$]⁺, [$C_6H_4$—O—$C_6H_4$—I—$C_6H_4$—O—$C_6H_4$]⁺, [$C_6H_4$—(C=O)—$C_6H_4$—I—$C_6H_4$—(C=O)—$C_6H_4$]⁺, [$C_6H_4$—I—$C_6H_4$—O—$CH_2$—O—$CH_2$—O—CH (OH)—$C_{12}H_{25}$]⁺, or a mixture thereof.

5. Initiator system according to claim 1, wherein the cyclic compound is selected from the group consisting of:

4,4'-dimethoxybenzoin; phenanthrenequinone; 2-ethylanthraquinone; 2-methylanthraquinone; 1,8-dihydroxyanthraquinone; dibenzoyl peroxide; 2,2-dimethoxy-2-phenylacetophenone; benzoin; 2-hydroxy-2-methylpropiophenone; 4-(2-hydroxyethoxy)phenyl-(2-hydroxy-2-methylpropyl) ketone;

benzoylacetone;

and a mixture thereof.

6. Composition which can be polymerized and/or crosslinked cationically under thermal or photochemical activation or under activation with a beam of electrons, comprising at least one monomer, oligomer and/or polymer containing organofunctional groups and at least one initiator system according to claim 1.

7. Composition according to claim 6, wherein the organofunctional groups are selected from the group consisting of epoxide, oxetane, alkenyl ether and acrylic groups.

8. Composition according to claim 6, wherein the monomers, oligomers and polymers containing organofunctional groups are polyorganosiloxane comprising units of formula (VII) and ending with units of formula (VIII), or cyclic comprising units of formula (VI), which are represented below:

in which:
the symbols $R^{17}$ are identical or different and represent:
a linear or branched alkyl radical containing 1 to 8 carbon atoms, optionally substituted with at least one halogen,
a cycloalkyl radical containing between 5 and 8 optionally substituted cyclic carbon atoms,
an aryl radical containing between 6 and 12 carbo atoms which may be substituted,
an aralkyl radical with an alkyl portion containing between 5 and 14 carbon atoms and an aryl portion containing between 6 and 12 carbon atoms, optionally substituted on the aryl portion with halogens, alkyls and/or alkoxys containing 1 to 3 carbon atoms;
the symbols Y' are identical or different and represent:
the group $R^{17}$,
a hydrogen radical,
and/or an organofunctional group which can be crosslinked cationically, connected to the silicon of the polyorganosiloxane via a divalent radical containing from 2 to 20 carbon atoms which can contain at least one hetero atom, and
at least one of the symbols Y' representing a functional organic group which can be crosslinked cationically; and
the symbol $R^{16}$, which may be identical or different, represents a radical selected from the group consisting of a radical $Ar^3$, a radical —(C=O)—$Ar^3$, a linear or branched $C_1$–$C_{12}$ alkyl radical, a $C_6$–$C_{12}$ cycloalkyl radical, wherein said radical is optionally substituted with one or more substituents selected from the group consisting of —F, —Cl, —Br, —CN, —OH, —CF$_3$, OR$^6$, —SR$^6$, —COOR$^6$, linear or branched $C_1$–$C_{12}$ alkyl radicals optionally bearing a group —OH, —OR$^6$, and/or —CN, and linear or branched $C_1$–$C_8$ alkenyl radicals.

9. Composition according to claim 8, wherein at least one of the symbols $R^{17}$ of the polyorganosiloxanes used represents a phenyl, tolyl or dichlosoppnnyl radical.

10. Composition according to claim 8, wherein the polymezizable, and/or crosslinkable composition also comprises additional monomers, oligamers and/or polymers containing organofunctional groups.

11. Composition according to claim 6, wherein the monomers, oligomers and/or polymers containing organofunctional groups belong to at least one of the following species:
$\alpha_{1.1}$ cycloaliphatic epoxides, taken alone or as a mixture with each other,
$\alpha_{1.2}$ non-cycloaliphatic epoxides, taken alone or as a mixture with each other,
$\alpha_3$ polyols, taken alone or as a mixture with each other, and
$\alpha_2$ linear or cyclic alkenyl ethers, taken alone or as a mixture with each other.

12. Composition according to claim 11, wherein the monomers, oligomers and/or polymers are selected from the group consisting of:
species $\alpha_{1.1}$ which is selected from the group consisting of 3,4-epoxycyclohexyl-methyl-3',4'-epoxycyclohexanecarboxylate and bis(3,4-epoxycyclohexyl) adipate;
species $\alpha_{1.2}$ which is selected from the group consisting of:
epoxides resulting from the coupling of optionally alkoxylated Bisphenol A and epichlorohydrin,
epoxides selected from the group consisting of 1,4-hexane-diol, glycerol, neopentyl glycol and trimethylolpropane,
Novolac epoxides, and
epoxidized and monohydroxylated, saturated or unsaturated diene polymers; and
species $\alpha_2$ which is selected from the group consisting of vinyl ethers, propenyl ethers and butenyl ethers.

13. Composition according to claim 6, which comprises monomers, oligomers and/or polymers containing an acrylic functional group.

14. Resin obtained from a composition according to claim 6.

15. Coating comprising the resin according to claim 14.

16. Coating according to claim 15, wherein the coating is a paint, an adhesive coating, an anti-adhesive coating and/or an ink.

17. Composite material obtained from a composition according to claim 6.

18. Object, at least one surface of which is coated with resin according to claim 14.

19. A method for the manufacture of coatings or composite materials comprising using an effective amount of the resin according to claim 14.

* * * * *